United States Patent
Su et al.

(10) Patent No.: US 6,855,197 B2
(45) Date of Patent: Feb. 15, 2005

(54) TOOTH CAVITY RESTORATION WITH NANOCOMPOSITE OF EPOXY RESIN AND NANOPARTICLES

(75) Inventors: Wei-Fang Su, Taipei (TW); Shih-Po Sun, Taipei (TW); Min-Huey Chen, Taipei (TW)

(73) Assignee: National Taiwan University, Taipei (TW)

( * ) Notice: Subject to any disclaimer, the term of this patent is extended or adjusted under 35 U.S.C. 154(b) by 28 days.

(21) Appl. No.: 10/379,661

(22) Filed: Mar. 6, 2003

(65) Prior Publication Data

US 2004/0162364 A1 Aug. 19, 2004

(30) Foreign Application Priority Data

Feb. 13, 2003 (TW) ........................................ 92103027 A

(51) Int. Cl.⁷ ............................. A61C 5/00; C08K 3/22; C08K 3/36; C09D 5/34
(52) U.S. Cl. ...................... 106/35; 433/228.1; 523/442; 523/443
(58) Field of Search ............................. 106/35; 522/77; 523/443, 442; 433/228.1

(56) References Cited

U.S. PATENT DOCUMENTS

| | | | |
|---|---|---|---|
| 3,066,112 A | 11/1962 | Bowen | |
| 5,730,601 A | 3/1998 | Bowman et al. | 433/228.1 |
| 5,998,495 A * | 12/1999 | Oxman et al. | 522/15 |
| 6,315,567 B1 * | 11/2001 | Hasel | 433/228.1 |
| 6,387,981 B1 * | 5/2002 | Zhang et al. | 523/117 |
| 6,572,693 B1 * | 6/2003 | Wu et al. | 106/35 |
| 6,620,864 B2 * | 9/2003 | Schmid | 523/457 |
| 6,730,156 B1 * | 5/2004 | Windisch et al. | 106/35 |
| 2003/0032693 A1 * | 2/2003 | Angeletakis et al. | 523/116 |

FOREIGN PATENT DOCUMENTS

| WO | WO 98/36729 | | 8/1998 |
|---|---|---|---|
| WO | WO01/30307 | * | 5/2001 |

* cited by examiner

Primary Examiner—Robert Sellers
(74) Attorney, Agent, or Firm—Troxell Law Office, PLLC

(57) ABSTRACT

A method of restoring a tooth cavity is conducted by a direct or indirect method with a visible light curable nanocomposite of a dental restorative material with a low polymerization shrinkage, wherein the dental restorative material comprises an epoxy resin, inorganic oxide nano particles, a photoinitiator and a photosensitizer. The direct method involves the filling of the tooth cavity with the nanocomposite dental restorative material, stacking the nanocomposite dental restorative material in the tooth cavity, and curing with visible light followed by shaping and polishing. The indirect method involves making a mold of the tooth, casting the mold with the nanocomposite dental restorative material, curing with visible light followed by shaping and polishing, then removing the shaped and polished material and adhering it to the tooth cavity.

8 Claims, 1 Drawing Sheet

TOOTH CAVITY RESTORATION WITH NANOCOMPOSITE OF EPOXY RESIN AND NANOPARTICLES

REFERENCE CITED
1. International Patent No.: WO 98/36729
2. U.S. Pat. No. 3,066,112

FIELD OF THE INVENTION

The present invention relates to a light curable nano composite material with low polymerization shrinkage used for restorative and esthetic dentistry.

BACKGROUND OF THE INVENTION

Commercial hybrid restorative composite such as Z100® (3M) and Tetric® Ceram(Vivadent) has been prepared by mixing organic polymer and inorganic fillers. Z100® for instance contains $ZrO_2$ and $SiO_2$ inorganic fillers of which the total content is 79% wt). The particle size is between 0.01 and 3.5 $\mu$m. The monomer matrix comprises Bisphenol-A glycidoxymethacrylates (Bis-GMA) and triethyleneglycoldimethacrylate (TEGDMA). Bis-GMA is the primary organic ingredient in nearly every commercial restorative resin. U.S. Pat. No. 3,066,112 to R. F. Bowen discloses a method of the synthesis of Bis-GMA, a monomer with two methacrylate functional groups and molecular weight about 512, from diglycidyl ether of bisphenol A (DGEBA) and methacrylic acid. Though the composite based on Bis-GMA has become major material for dental restoration due to its superior aesthetic quality, simple operation technique and enhanced mechanical strength, there are still problems. Volumetric shrinkage ranging from 2.6% to 7.1% after curing causes microleakage, a well-known effect of contraction gaps on the interface of resin and tooth. Saliva, fluid, food residue and microorganism trapped in the gaps lead to decayed tooth and damaged material, which is the major problem in nowadays restorative and esthetic dentistry. Therefore it is our object to provide a material with satisfactory mechanical properties and low polymerization shrinkage.

Joachim in Pat. No. WO 98/36279 discloses the use of highly branched methacrylate macro monomer, of which the molecular weight is from 2000 to 25000 g/mol, as the polymerizable resin. The high molecular weight polymerizable resin has fewer functional groups than that of low molecular weight monomer. The curing contraction is due to the reduction of free volume obtained from polymerization of functional groups. Therefore, the contraction can be reduced using high molecular weight monomer. However increasing molecular weight of monomers is combined with an increasing viscosity of the monomer and this makes it difficult to apply in clinic. Bowman in U.S. Pat. No. 5,730,601 discloses the use of mixing poly(ethylene glycol) dimethacrylate (PEGDMA) of which the molecular weight is from 600–800 g/mol and Bis-GMA as organic monomers. The long chain lowers the number of functional groups in molecule. However the poly(ethylene glycol) structure can easily twist and plasticize the cured resin to reduce their mechanical strength. The polymerization shrinkage consequently cannot be effectively reduced if monomers with methacrylate functional groups were used. A need exists therefore, for a resin monomer with less curing contraction to replace those with methacrylate groups as monomer sources. The object of the invention Is to provide a material with satisfactory mechanical properties, convenient operational techniques and respectively low polymerization shrinkage.

SUMMARY OF THE INVENTION

The present invention relates to a new light curable dental restorative composite material with a low polymerization shrinkage used for adhesion, casting, filling, coating and restoration in clinical dentistry. After the preparation of the material outside of the oral cavity, it can be further cured in oral cavity by visible light or implanted into the oral cavity after curing outside the oral cavity.

BRIEF DESCRIPTION OF THE DRAWINGS

The present invention may best be understood through the following description with reference to the accompanying drawing.

DETAILED DESCRIPTION OF THE PREFERRED EMBODIMENT

Figure 1:
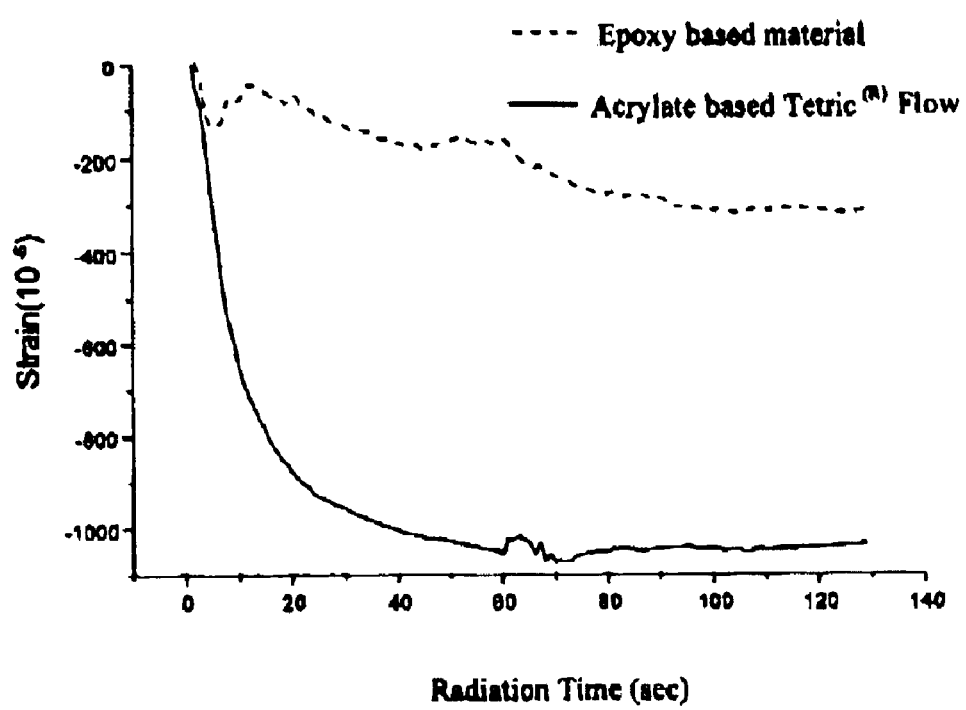
FIG. 1 is a diagram showing the relation of the shrinkage strain to the curing light radiation time.

The present invention will now be described more specifically with reference to the following embodiments. The process to create the light curable epoxy nano composite dental restorative material with a low polymerization shrinkage used for restorative and esthetic dentistry described in the present invention comprises:

a) mixing the inorganic oxide nano particles with surface modification solution b) mixing the surface modified inorganic oxide nano particles with the light curable dental epoxy resin.

Furthermore, the method of usage for the present invention for tooth cavity restoration includes direct or indirect methods:

The direct method:

a) filling the light curable nano composite dental restorative material with a low polymerization shrinkage into the prior prepared tooth cavity.

b) stacking of the light curable nano composite dental restorative material with a low polymerization shrinkage in the tooth cavity;

c) applying curing light to initiate the polymerization process of the light curable nano composite dental restorative material with a low polymerization shrinkage;

d) shaping and polishing of the light curable nano composite dental restorative material with a low polymerization shrinkage after the curing process, The indirect method:

a) molding of the decayed tooth after the cavity preparation;

b) casting of the mold with the light curable material with low polymerization shrinkage;

c) applying curing light to initiate the polymerization process of the light curable nano composite dental restorative material with a low polymerization shrinkage;

d) shaping and polishing of the light curable nano composite dental restorative material with a low polymerization shrinkage after the curing process; and e) removing of shaped and polished resin from the mold and adhere it to the tooth cavity of the patient.

The present invention will further be described in more detail. There are three steps to be taken to prepare dental restorative material with a low polymerization shrinkage. The first step is to prepare inorganic oxide nano particles. The second step is to mix the inorganic oxide nano particles with epoxy resin. The third step is to initiate the ionic polymerization with curing light to form the hardened dental restorative material with a low polymerization shrinkage.

The inorganic oxide nano particles mentioned in the first step have a general formula of $MO_x$, where in M is the inorganic element or a mixture of different inorganic elements, selected from the group consisting of Si or Zr, and where in x being determined by the ionic valence number of the element. The particles comprise of particles with average particle size less than 500 nm or particle mixture with different sizes less than 500 nm. They can be prepared by the sol-gel method which includes hydrolysis and condensation of metal alkoxides, for example $Si(OC_2H_5)_4$. There are also different kinds of commercial products to be used directly including MA-ST-M Colloid Silica (Nissan Chemical Co.) or IPA-ST-M Colloid Silica (Nissan Chemical Co.). The surface of inorganic oxide nano particles can be further modified organically to improve the dispersion and stability of inorganic oxide particles in epoxy matrix or to increase the bonding force between particles and matrix. Organic modification utilizes alkoxysilanes with organic functional groups having the general formula $(Y-R)_n SiX_m$, where in Y is selected from the groups which can react with epoxy group such as another epoxy group. Y is also selected from the groups which cannot react with epoxy group consisting of benzene or alkyl, and wherein $n=1$, 2 or 3, $n+m \leq 4$. In order to connect and separate Y and Si atom, R is an alkyl chain on which there are preferably 5 or more carbon atoms. X is the group which can become the Si—OH group through hydrolysis consisting of alkoxide or halogen. The silanes for surface modification is selected from the group consisting of diphenyldimethoxysilane or γ-glycidoxypropyltrimethoxysilane (Z-6040, Product of Dow Corning). After the hydrolysis of the silane for surface modification under acid or base catalysis, it was then mixed with the aforementioned inorganic oxide particles under temperature between 40 to 80° C. for over 10 hours forming solutions with surface modified inorganic oxide particles.

In the second step, the solution containing inorganic oxide nano particles from step one will be mixed together with the epoxy resin monomer, the photoinitiator and the photosensitizer. The epoxy resin monomer is selected from the group consisting of aliphatic, cycloaliphatic and aromatic. The preferred embodiment of the epoxy resin monomer is cycloaliphatic epoxy with more than one epoxide group and the preferred embodiment is two. Many commercial epoxy resins can be used, for example 3,4-epoxycyclohexanemethyl-3,4-epoxycyclohexane carboxylate (ERL-4221, Union Carbide) or 4-vinyl cyclohexene dioxide (ERL-4206, Union Carbide). The selection of suitable ionic polymerization photoinitiator depends on different epoxy resin monomers. The photoinitiator is selected from the group consisting of diaryliodonium, triarylsulfonium and ferrocenium salts. The preferred embodiment is the diaryliodonium salts, for example (4-octylphenyl) phenyliodonium hexafluoroantimonate (OPIA, General Electric Co.). The absorption wavelength of the photosensitizer has to be in the visible light spectrum. The preferred embodiment of the wavelength is from 400 nm to 600 nm and adequate quantum yield appears in this range. The preferred embodiment of photo sensitizer is camphorquinone. The photosensitizer and initiator need to be dissolved in epoxy resin monomer. The preferred embodiment of composite can be prepared from the following weight percent range: photoinitiator:photo sensitizer:epoxy resin= 0.01–0.02:0.02–0.05:1. After the mixing of these three components with the solution containing the inorganic oxide nano particles prepared in step one, solvents such as water and alcohol are then removed under low pressure at 40–60° C. without light exposure to make visible light curable composite epoxy resin.

In the third step, the visible light curable epoxy resin prepared in step two can be cured by people familiar with the polymer processing or dentists familiar with the procedures of tooth cavity restoration. For example, by using dental curing lamp with a wavelength over 400 nm such as Optilux® 401 Curing Light (Kerr Co.) for several seconds up to several minutes, the resin can be hardened as thin film or bulk material.

EXAMPLE ONE

Preparation of ERL4221-$SiO_2$ Composite Resin 3.24 g of ethanol and 1 g of water were mixed and 35% hydrochloric acid were added until the solution reaches pH=3.5. 1 g (4.23 mmol) of γ-Glycidoxypropyltrimethoxysilane (Z-6040, Dow Corning) was dissolved in the solution and stirred for 20 minutes at 50° C. Afterwards 10 g of colloid silica particles (MA-ST-M, Nissan Chemical) with an average particle size of 20–25 nm, was added dropwise. The solution was stirred for 10 hours at 50° C. and then it was cooled to room temperature and stops stirring.

20 g of 3,4-Epoxycyclohexanemethyl-3,4-epoxy-cyclohexanecarboxylate (ERL-4221, Union Carbide) and 0.8 g of (4-Octylphenyl) phenyliodonium hexafluoroantimonate (UV-9380C, General Electric Co.) 0.4 g of camphorquinone were dissolved in the aforementioned solution and kept from light exposure, The solvent of the mixed solution is then removed under vacuum to obtain ERL4221-SiO2 composite resins. They are stored under room temperature and away from light for further testing.

EXAMPLE TWO

Preparation of Bulk Specimen

Bulk specimens were prepared by filling 6 mm in diameter and 2 mm in thickness Teflon mold with the composite resin and then covered with Mylar strips on each side between two glass slides. After 60 seconds exposure of curing light with 400 nm–500 nm in wavelength and 700 mW/cm$^2$ intensity, the specimen and the mold were kept in 37° C. for 24 hours. The hardened specimen was then removed for testing.

EXAMPLE THREE

Characterization of the Composite Resin a) Hardness Measurement

Microhardness was measured using Knoop hardness indenter HMV Hardness Tester (SHIMADZU) with a 98.07 mN load for 10 sec. At least 5 different points were tested on one specimen and the results were shown in Table 1.

TABLE ONE

| Knoop hardness values | |
| --- | --- |
| Material | Hardness (KHN) |
| Specimen | 38.0 |
| Z-100 ® (3M) | 37.5 | b) Comparison of Polymerization Shrinkage

The polymerization shrinkage was measured by strain gauge method. The instruments used were a Measurements Group Inc. MODEL 3800 strain meter and a KYOWA KFRP-5-120-C1-6 strain gauge. The strain gauge was stick to a silicon pad with 7 mm in thickness by using cyanoacrylate type instant glue. Afterwards, composite for testing was poured on the gauge until the circuits on the top of the gauge was fully covered by the resin with a thickness of about 1 mm. The light source was above the resin with a distance in between of about 2 mm and the strain gauge indicator was reset to zero. The curing light was turned on for 60 seconds. The strain variation was then recorded from the beginning of irradiation until the variation stops changing. The results are shown in FIG. 1. It is evident that the shrinkage of the material composed of epoxy resin is 50% lower than that of materials using acrylic resin as the organic matrix. It therefore is a dental restoration material with a low polymerization shrinkage. Additionally, the inorganic oxide nano particles can comprise silicon dioxide, zirconium dioxide or their mixtures to create inorganic oxide nano particles with an average size of less than 100 nm. The compression strength of the light curable dental restorative material with a low polymerization shrinkage after the hardening process is larger than 35 Mpa, the surface hardness is larger than 35 KHN.

The ability of the light curable dental restorative material provided by the present invention to reduce the polymerization shrinkage of dental restoration materials is proven, it thus not only provides an improvement but also breaks the current limits of technology, and is all together an invention of very progressive character.

Furthermore, the present invention can also be used in various areas of restorative and esthetic dentistry, and is therefore an invention of very practical character.

To sum up the above mentioned, the present invention is inventive, innovative and progressive. The patent for this present invention is hereby applied for. It should include all variations and versions covered by the present invention, including possible minor improvements and more exact definitions.

The above mentioned practical examples are used to describe the invention in more detail, they should therefore be included in the range of the invention, but should not restrict the invention in any way.

What is claimed is:

1. A method of restoring a tooth cavity via a direct or indirect method with a visible light curable nanocomposite of a dental restorative material with a low polymerization shrinkage, wherein th dental restorative material comprises an epoxy resin, inorganic oxide nano particle, a photoinitiator and a photosensitizer;
   a) said direct method including the steps of:
      i) filling the light curable nano composite dental restorative material with a low polymerization shrink into the prior prepared tooth cavity;
      ii) stacking of the light curable nano composite dental restorative material with a low volvme polymerization shrinkage the tooth cavity;
      iii) applying curing visible light to initiate the polymerization process of the light curable nano comooste dental restorative material with a low polymerization shrinkage; and
      iv) shaping and polishing of the light curable nano composite dental restorative material with a low polymerzation shrinkage after the curing process; and
   b) said indirect method including the steps of:
      i) making a mold of the tooth after the cavity preparation;
      ii) casting of the mold with the light curable nano composite dental restorative material with low polymerization shrinkage;
      iii) applying curing visible light to initiate the polymerization process of the light curable nano composite dental restorative material with a low polymerization shrinkage;
      iv) shaping and polishing of the light curable nano composite dental restorative material with a low polymerization shrinkage after the curing process; and
      v) removing of shaped and polished nano composite dental restoarative material from the mold and adhering it to the tooth cavity of the patient.

2. The method according to claim 1, wherein said low polymerization shrinkage is at least 50% lower in comparison with dental restoration materials based on acrylic resin matrix.

3. The method according to claim 1, wherein said inorganic oxide nano particles are selected from a group consisting of silicon dioxide, zirconium dioxide and their mixtures.

4. The method according to claim 1, wherein an average size of said inorganic oxide nano particles is less than 100 nm.

5. The method according to claim 1, wherein an average aggregated size of said inorganic oxide nano particles is less than 500 nm.

6. The method according to claim 1, wherein said epoxy resin contains at least two epoxy groups per epoxy resin monomer.

7. The method according to claim 1, wherein an compression strength after the hardening process of said light curable epoxy nano composite is larger than 35 Mpa.

8. The method according to claim 1, wherein a surface hardness after the hardening process of said light curable epoxy nano composite is larger than 35 KHN.

* * * * *